(12) United States Patent
Mellard

(10) Patent No.: US 9,878,088 B2
(45) Date of Patent: Jan. 30, 2018

(54) APPARATUS FOR SUPPORT OF PATIENTS AND MEDICAL FLUID LINES

(71) Applicant: Steven Mellard, Atlanta, GA (US)

(72) Inventor: Steven Mellard, Atlanta, GA (US)

( * ) Notice: Subject to any disclaimer, the term of this patent is extended or adjusted under 35 U.S.C. 154(b) by 0 days.

(21) Appl. No.: 15/218,816

(22) Filed: Jul. 25, 2016

(65) Prior Publication Data

US 2017/0021092 A1 Jan. 26, 2017

Related U.S. Application Data

(60) Provisional application No. 62/196,278, filed on Jul. 23, 2015.

(51) Int. Cl.
*A61M 5/14* (2006.01)
*B60B 33/00* (2006.01)

(52) U.S. Cl.
CPC ....... *A61M 5/1415* (2013.01); *B60B 33/0089* (2013.01); *B60B 33/0092* (2013.01); *B60B 2200/26* (2013.01)

(58) Field of Classification Search
CPC . A61H 3/04; A61H 2003/046; A61M 5/1415; A61M 5/1417; A61M 5/1418; A61M 5/1414; A61G 12/008; A61G 7/0503; A61G 2203/80; F16M 11/28; B60B 33/0089; B60B 33/0092; B60B 2200/26
USPC ...... 280/47.34, 47.35, 47.371, 200; 248/121, 248/125.1, 125.2, 125.3, 125.7, 125.8, 248/125.9, 129, 158, 161
See application file for complete search history.

(56) References Cited

U.S. PATENT DOCUMENTS

| | | | | |
|---|---|---|---|---|
| 5,865,065 A * | 2/1999 | Chiu | ...................... | B62L 3/02 74/489 |
| 7,624,953 B2 * | 12/2009 | Silverman | ........... | A61M 5/1415 248/125.1 |
| 7,735,789 B2 * | 6/2010 | Blankenship | ........ | A61G 7/0503 248/129 |
| 7,918,422 B2 * | 4/2011 | Blankenship | ....... | A61M 5/1415 248/129 |
| 2002/0096608 A1 * | 7/2002 | Cedarberg, III | ..... | A61M 5/1418 248/125.3 |
| 2007/0267550 A1 * | 11/2007 | Blankenship | ........ | A61G 7/0503 248/125.8 |
| 2009/0085317 A1 * | 4/2009 | Livengood | ............... | A61H 3/04 280/79.3 |
| 2013/0292521 A1 * | 11/2013 | Chepurny | ............ | A61G 12/008 248/97 |

* cited by examiner

*Primary Examiner* — Patrick Hawn
(74) *Attorney, Agent, or Firm* — F. Russell Denton; Denton Intellectual Property Law Firm

(57) ABSTRACT

The invention provides a medical intravenous support apparatus that facilitates patient mobility while reducing the likelihood of an accidental fall. The design incorporates improved features for bag support, tube management, cord management, patient steadiness, user-friendly braking, and electric power supply.

12 Claims, 8 Drawing Sheets

RAISED MAST          LOWERED MAST

RAISED MAST                LOWERED MAST

RAISED MAST

LOWERED MAST

APPARATUS FOR SUPPORT OF PATIENTS AND MEDICAL FLUID LINES

RELATED APPLICATIONS

This invention derives priority from a provisional U.S. patent application Ser. No. 62/196,278, having the same inventors, filed Jul. 23, 2015 and entitled "A Structure to Improve the Mobility and Safety of Medical Patients".

FIELD OF THE INVENTION

The invention pertains to devices for intravenous administration and physical support for patients.

BACKGROUND

Intravenous (IV) devices date back to 1831, when Dr. Thomas Latta treated a choleric elderly Englishwoman with an IV injection to "throw the fluid immediately into the circulation". There a vessel containing the fluid was held manually. Today IV infusion therapy is used routinely when fluid administration by another route might be physiologically less effective or simply less convenient for health care professionals. Modern infusion vessels for IV fluids are typically supported by a pole or a stand.

Mobile designs for IV stands are used widely to facilitate patient mobility, particularly in light of recent findings that early ambulation improves patient recovery times and reduces the length of their hospital stays. Yet greater mobility of these IV stands has also been associated with increased risk of in-hospital falls by the patient. Medicare and insurance are not required to cover the cost of treatment arising from such falls, yet by law hospitals and care facilities are responsible for those costs. The average per-patient cost for care after a patient's in-facility fall is $13,316 more than for comparable patients who have not fallen. See: Fisher et al., "Early Ambulation and Length of Stay in Older Adults Hospitalized with Acute Illness," *Archive of Internal Medicine*, 170:21 (National Institutes of Health, U.S. National Library of Medicine, Nov. 22, 2010); risk factors in Anonymous, "Understanding Fall Risk Prevention and Protection," posted at www.sizewise.net/getattachment/2d5c6915-509c-4d99-a653-bef8bcc56fdc/sw-fall-risk-toolkit.aspx; Ganz et al. "Preventing Falls in Hospitals: A Toolkit for Improving Quality of Care," (Agency for Healthcare Research and Quality, January 2013).

In addition to fall-related hazards, the current design of IV poles is less than ideal for patients in other ways. The pole has a tall mast, the crown of which bears a load of fluids and commonly tips over. Often a single pole has a multitude of IV bags, each for a different drug to treat the hospitalized individual. Each bag has its own tubing to supply the implant on a person's arm. The tubes are cumbersome, may tangle, and sometimes yank the implant from a patient's arm when the stand topples. The addition of sensors, medicines and monitors to the pole adds to the apparatus weight and difficulty of control by patients.

The IV pole designs have disadvantages for nursing as well. Nurses in units for surgery, intensive care, and emergency care commonly criticize the designs as inconvenient due to their bulk, excessive height, large size of base footprint, tipping hazard, poor ergonomics, entanglement of cord and tubing, and lack of user-friendliness for patients who need to slow or stop a traveling pole. The prior art contains a variety of attempts to improve pole designs.

U.S. Pat. No. 2,627,431 A, issued 3 Feb. 1953 to Sechrist, provides methods for attaching a collar to a pole.

U.S. Pat. No. 3,929,210 A, issued 30 Dec. 1975 to Morris et al. teaches use of a spring to retract tubing, cord and or wire.

U.S. Pat. No. 5,865,065 A, issued 2 Feb. 1999 to Chiu, discloses use of a mechanical hand brake for use in walking aids.

U.S. Pat. No. 4,892,279 A, issued 9 Jan. 1990 to Lafferty et al. incorporates a folding tripod feature to facilitate portability of IV stands by allowing quick collapse and redeployment.

U.S. Pat. No. 6,585,683 B2, issued 19 Sep. 2001 to Sutton et al., discloses a structure with a form-fitting clip to hold a single tube.

US Pub. Pat. App. No. 2004/0144673 A1 by Mark Buczek, published 29 Jul. 2004, provides passages in a surgical tray to take up slack in surgical tubing in an operating room.

U.S. Pat. No. 8,313,066 B2, issued 20 Jun. 2012 to Hampton et al., discloses a quick-release system for wheels of an IV stand, and employs a plurality of casters.

U.S. Pat. No. 9,010,709 B1, issued 21 Apr. 2015 to Culpepper et al., teaches use of a ceiling-mounted articulated arm with an electromagnetic braking system to control the momentum of a suspended structure.

Although features of several of those inventions are in common use today, the contemporary design of mobile IV support devices continue to suffer from the disadvantages discussed above. Thus there is an ongoing need for improvements in their design.

SUMMARY OF THE INVENTION

The invention provides a medical intravenous support apparatus that facilitates patient mobility while reducing the likelihood of an accidental fall, and can be used in addition or alternatively for support of components for catheterization or other types of fluid transfer lines. The design incorporates improved features for bag support, tube management, patient steadiness, user-friendly braking, and electric power supply.

In a particular embodiment the invention provides an apparatus for support of components for transfer of fluids to or from medical patients, comprising:
  a) a caster module wherein:
    i) three or more casters are distributed about the caster module symmetrically relative to each other and equidistant from a virtual central point of the caster module;
    ii) a receiving collar defines a central passage through the caster module, wherein that passage is symmetrically distributed about a virtual center line that is defined by virtual central points of cross-sections of the passage when the caster module is horizontal; and
    iii) the receiving collar is configured to receive and hold a mast in an upright orientation when the casters rest on a horizontal floor surface;
  b) an upright center mast wherein:
    i) the mast passes through and is slidably connected to the receiving collar of the caster module;
    ii) the bottom of the mast is mated with one or more feet and said one or more feet reside below the receiving collar of the caster module when the casters rest on a horizontal floor surface;
    iii) one or more peripheral handles are mounted on a central portion of the mast, wherein:

A) at least one peripheral handle defines at least one channel for receiving at least one tube or power cord; and B) at least one power outlet is mounted on the center mast; and iv) a crown is mounted at the top of the mast and comprises a plurality of supports for hanging, wherein each of at least two of said supports for hanging have sufficient strength to support at least one full bag of an intravenous fluid; and c) the support apparatus further comprises a brake assembly comprising:

i) at least one hand brake handle, wherein at least one of the central portion of the mast and a peripheral handle has a hand brake handle mounted upon it;

ii) a brake for application to at least one of a floor surface and a caster; and iii) a brake line that is connected to each of the hand brake handle and the brake.

DETAILED DESCRIPTION OF THE INVENTION

Figure 1:
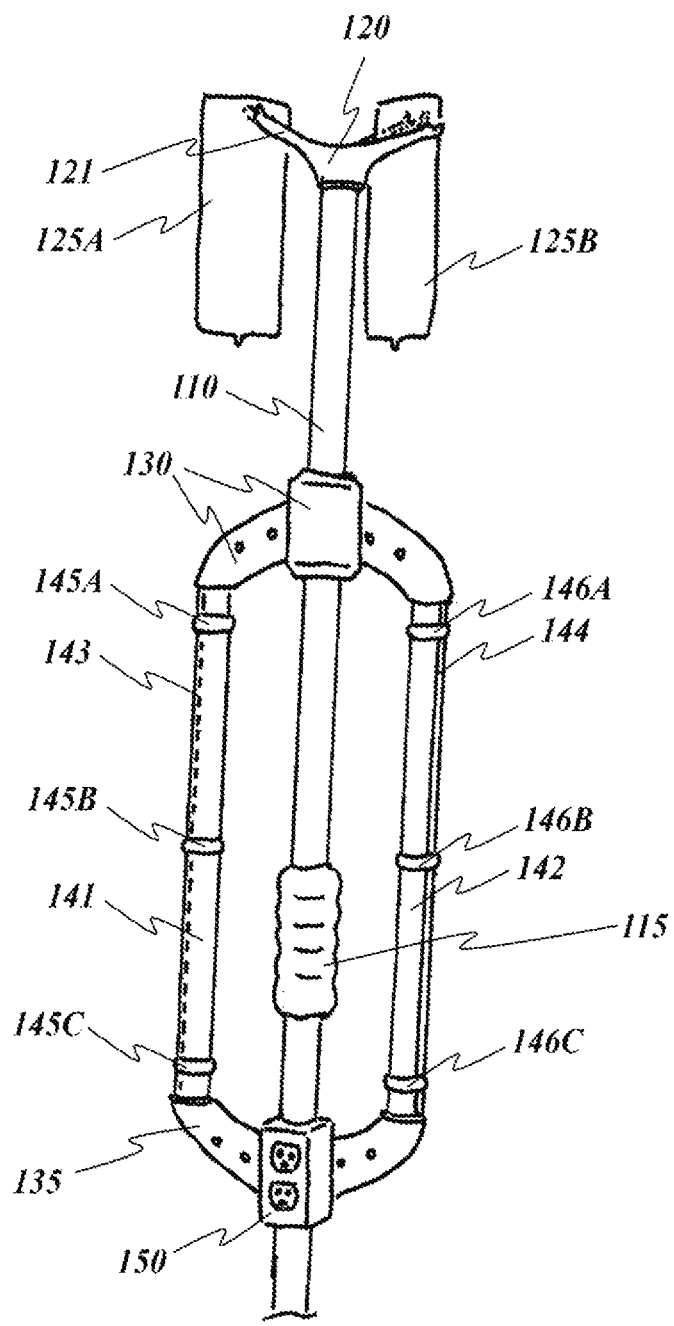
FIG. 1 is a caricature depicting a non-limiting embodiment of the invention comprising the top half of the stand, a crown, hooks, vertical handles defining channels, retaining rings for tubing retention, a handgrip and power receptacles.

The invention may be further understood by a consideration of the following definitions for terms as used herein.

The terms "apparatus", "support apparatus" and "assembled apparatus" are used interchangeably and mean the entire device according to the invention.

The term "components for transfer of fluids to or from medical patients" as used with respect to components, means items useful for the delivery of fluids to or from medical patients, and includes but is not limited to bags such as are used for saline fluids, medicament-containing fluids, blood and platelets; tubes for transferring fluid between bags and needles; needles for intravenous delivery of fluids; catheters; and the like.

The term "transfer of fluids" as used with respect to components means that the fluids are delivered to or from the body of a medical patient.

The term "medical patient" means a patient for whom therapeutic or preventative treatment is being provided by means of a transfer of fluids. The term patient includes but is not limited to human patients, and may also include other mammals such as dogs, cats, primates, livestock, and may also include birds and fish that are medical patients.

The term "apparatus" means a device, and in particular a device that is capable of providing physical support simultaneously both for components for transfer of fluids and for a medical patient.

The term "caster" refers to a rolling element and may include but is not limited to a type of caster such a ball caster, wheel caster, bolt hole caster, leveling caster, plate caster, pneumatic caster, side-mount caster, or stem caster.

The term "caster module" means a base for supporting an apparatus, wherein the base is attached to and can be supported by one or more casters.

The term "distributed about the caster module symmetrically relative to each other," as used with respect to a plurality of casters means that they are placed symmetrically across opposite sides of a line and/or that the plurality of casters is placed such that their locations at regular intervals around a circle.

The term "equidistant from a central point of the caster modules," as used with respect to a plurality of casters, means that they are placed around a circle and at a relatively constant distance from a point at its origin, i.e., at the center of the circle.

The term "receiving collar" means the perimeter of an orifice in the caster module having a sufficient size, shape and materials strength such that when the module is upright and resting on an essentially horizontal surface and a suitable mast is inserted into the orifice, the mast can be held essentially erect.

The term "central passage" means the orifice in the caster module that is surrounded by the perimeter referred to as the receiving collar. The term "virtual central point" as used with respect to a central passage means the center of a cross-section of the passage. The term "virtual center line" as used with respect to a central passage means the line defined by the virtual central points as defined by two or more cross-sections of such a mast.

The terms "mast" and "center mast" are used interchangeably and mean a beam such as a rod, post, beam, spar, tube, combined rod-in-tube, or other structure useful for vertical support. As the term is used herein a mast may have a cross-section that is circular, triagonal, square or otherwise rectangular, or otherwise polygonal, or star-shaped with three or more vertices, or another shape, or may vary along the length of the mast. In some embodiments the cross-section of mast is constant but twists in orientation along the length of the mast. In some embodiments the mast is contoured at one or more areas on its surface in a way that provides ridges, cross-hatches, notches, bumps or other features that improve the ability to be gripped by a human hand or held by a handle such as a rubber, plastic or metal handle for gripping by a human hand.

The term "vertically mobile relative to the caster module", as used relative to the center mast, means that the mast may be moved in upward and downward directions while the caster module remains stationary.

The term "pneumatic" as used with respect to components has its usual and ordinary sense in mechanical engineering. The terms "first site" and "second site" as used with respect to a pneumatic component refer to portions of that component that are mobile relative to each other.

The term "configured to receive and hold," as used with respect to a receiving collar relative to a mast, means that the mast fits within the orifice in the receiving collar, with sufficiently close tolerances that the mast is held upright. The receiving collar may have grooves and or ridges that are complementary relative to respective corresponding ridges and or grooves of the mast. In some embodiments the receiving collar and or the mast may be lined on one or more of the mated surfaces with a composition that possesses high friction when pressure is applied. In further embodiments the receiving collar and or the mast may contain a brake actuation lever that is engaged when downward pressure is applied to the mast.

The terms "upright orientation" and "upright" as used with respect to a mast are interchangeable and mean that the mast is held at a relatively fixed orientation. In some embodiments the orientation angle is different from vertical and the angle falls within a range for which the outer value in degrees is: 0, 5, 10, 15, 20, 25, 30, 35, 40, 45, 50, 55, 60, 65, 70, 75, 80, 85, 90, 95, 100, 105, 110, 115, or 120 degrees.

The "passes through" as used with respect to a mast and a receiving collar means that the mast is inserted into the orifice defined by the receiving collar.

The term "slidably connected as used with respect to a mast and a receiving collar means that when the mast passes through the receiving collar the mast retains significant freedom to slide along the pass-through direction relative to the receiving collar.

The term "bottom" as used with respect to a mast means the lowermost portion of the beam of a mast. In certain embodiments the mast may be split at the bottom to form legs, or may have legs otherwise attached at the bottom.

The term "foot" or "feet" as used with respect to a mast means a feature such as a cap, plug or appendage that may be affixed at or near the bottom of the mast or if present, at or near the bottom of a leg of the mast. In particular embodiments a foot is composed of a friction-enhancing material such as rubber, leather, a textile, or another friction-enhancing material.

The term "mated" as used with respect to a foot on a mast means attached, such as for instance, a cap inserted over and around the bottom of a beam, a protruding plug inserted into a hollow bottom end of a beam, an appendage affixed to a side near the bottom of a beam, irrespective of whether the beam is a simple beam or has legs. In particular the mating may be assisted by means of a device such as a screw, bolt, rivet, clamp or other attachment means.

The term "horizontal floor surface" means a surface such as the floor of a building, irrespective of whether the surface composition is wood, concrete, laminated material, ceramic, textile, or another composition.

The term "rest" as used with respect to a caster on a floor surface means that a rollable portion of the caster is in contact with the floor surface, irrespective of whether the rollable portion is braked or not.

The term "central portion of the mast" as used with respect to the location of a mounted component means that the component is mounted within a region of the mast that is intermediate between the caster module and a crown at the top of the mast.

The term "peripheral handle" means a feature that is attached to but extend away from a center mast. In illustrative non-limiting embodiments a peripheral handle has a configuration such as: forming a "D" shape with the center mast; extending horizontally from the center mast; forming a horizontal circle about the center mast, with attachment by braces to the center mast; linear and parallel to the center mast, with attachment by braces to the center mast; linear and orthogonal to the center mast, with attachment by braces to the center mast; and variations and combinations of the same.

The term "mounted" and "affixed" as used with respect to one component on another means that they are attached. In certain embodiments the attachment is permanent; in alternative embodiments it is susceptible to piecemeal manual disassembly and reassembly; in still other embodiments it affords quick-release disassembly and reassembly, illustrative non-limiting examples of the attachment include by means of a weld, screw, bolt, rivet, adhesive, male and female features of the handle and mast, paired hook-and-loop fabrics, suspension on one or more hooks, and friction fit. The terms mounted and affixed as used herein contemplate that one or more braces for a component may be the portion attached to another component.

The term "channel" as used with respect to a handle means that the handle has a hollow portion running for some length through it suitable for holding an intravenous tube or power cord. In particularly preferred embodiments the proportions and configuration of the handle and channel are such that an intravenous tube or power cord may be inserted into the channel manually and quickly, and supported by the channel without falling when the assembled support apparatus is upright. In particular embodiments the channel has a slot running along one side, where the slot is wide enough to insert a zone of tube or power cord through the slot. In some embodiments the slot is marginally narrower than the tube or power cord, such that either must be manually squeezed in order to fit through a slot. In certain other embodiments the slot is located on the upper half of a channel and sufficiently wide that no squeezing of the tube or power cord is necessary to insert them. In still other embodiments the handle is composed of a flexible material and a slit or slot along the length of a channel is pried open to allow insertion of the tube or power cord. In still other embodiments the channel is located at the interface between the handle and a brace or center mast, and the handle is of a type that may be quickly removed and replaced.

The term "define" as used with respect to a channel defined by a handle means that a channel is located within the handle.

The term "receive" as used with respect to a tube or power cord in a channel means that the channel has proportions and a configuration suitable for reversible placement of the tube or power cord into the channel.

The term "power outlet" means a feature having at least one electrical receptacle bearing at least one socket that has a design suitable for mechanically engaging with and supplying electricity to the plug of a power cord. In some embodiments the outlet is powered by electrical current from a cord that runs to a wall receptacle. In certain embodiments the outlet is alternatively or additionally powered by electrical current from a battery. In particular embodiments multi-socket outlets are mounted both above and below peripheral handles. In certain embodiments a power outlet is mounted at a sufficient distance and orientation relative to a hand brake handle that a user of the upright apparatus is unlikely to grasp the outlet when he or she needs or intends to grab the hand brake handle instead. In certain embodiments a power outlet is supplied by an electrical line for which a length is located within a tubular center mast; in various other embodiments a power outlet is supplied by an electrical line for which a length is located outside but attached to a center mast The term "crown" means a feature that is located at the top of or above a center mast, and affixed to that center mast, and that comprises at least two supports for hanging. The crown may be in the form of arms that extend upward and or outward. Alternatively the crown may be a circular, polygonal, star-shaped or other shaped component that is attached directly or by means of braces to the center mast. The crown may optionally comprise several parts, for instance where a plurality of arms are individually and independently attached at or near the top of the center mast. The terms "arm" and "hook" as used with respect to a crown are used in a general sense and do not limit the exact shape of those respective components. In general a hook may be regarded as having some portion that curls back on itself while an arm may be regarded as having some portion that does not curl back on itself but extends outward and or upward. Some components may be regarded as having both an arm and a hook. And some arms may be regarded as being hooks as well, and vice versa.

The term "support for hanging" means a feature that is suitable for use in suspending an intravenous bag by its top end. Illustrative nonlimiting examples of support for hanging include arms, hooks, clips, clamps, straps and cords for tying. The term "support for hanging" contemplates optional use of a feature such as a carabiner or key-ring type of clip to attach a fixed component of the crown to an orifice in the sealed top margin of an intravenous bag.

The term "brake" means a component for inhibiting lateral motion of the upright assembled apparatus. In some embodiments a brake is applied by introducing friction between the apparatus and a floor surface. In certain embodiments a brake is applied by introducing friction to restrict motion at one or more casters. Illustrative nonlimiting examples of brakes for apparati according to the invention include a cap on the bottom of a center master where the cap may be pressed against a floor surface; an actuatable clamp for a caster; and a compressible housing for a caster.

The term "brake assembly" means all components involved braking and its actuation, including a hand brake handle, a brake line for conveying mechanical force and or electrical signals to actuate a brake, and the brake itself.

The term "hand brake" means a brake that may be actuated manually. Non-limiting illustrative examples include: pushing down on a center mast to initiate contact between a friction-providing foot and a floor surface; squeezing a handle on a mast to actuate brakes on casters; turning a lateral handle in a mast having a rod-in-a-tube configuration, such that turning the handle outward or alternatively inward lowers the rod such that a foot at the bottom of the rod comes into contact with a floor surface; and pushing down on a peripheral handle to apply pressure to one or more casters below, thereby actuating a brake at the one or more casters.

The term "handle" as used with respect to a hand brake means a handle by means of which the brake may be actuated manually.

The term "brake line" means the series of physically connected components through which brake actuation is necessarily performed. By way of an illustrative nonlimiting example, where a brake is applied by means of pushing a foot of a central mast against a floor surface the brake line is the central mast. Another such example is where a peripheral handle is pushed downward to apply a brake at a caster by compression of the caster housing against a wheel: There the brake line is the center mast, the caster module, a shock absorber if present at the caster, and—to the extent the caster housing is not regarded as part of the brake at that caster—also includes the caster housing exclusive of the zone or composition that serves as the braking material.

The term "engagement mechanism" as used with respect to a brake means the mode of actuation by which by which a user's pressure or motion at a hand brake handle applies the brake. In certain embodiments the mechanism is strictly mechanical in nature. In certain other embodiments the mechanism is by means of an assembly comprising one or more electrical components.

The term "downward force" means force or pressure applied in a substantially downward direction. The downward direction may be orthogonal to a floor surface or at some other angle relative to a floor surface, such as at a number of degrees falling within a range for which the outside value is 85, 80, 75, 70, 65, 60, 55, 50, 45, 40, 35 or 30 degrees relative to a horizontal floor.

The term "critical threshold" as used with respect to the amount of force required to actuate a brake means the minimum amount of force or pressure that must be applied at the hand brake handle to engage the brake. In some embodiments of the invention the critical threshold is adjustable by the user, such as where a user is substantially lighter, substantially heavier, substantially weaker or substantially stronger or has substantially worse or better balance than an average range for intravenous patients. In certain embodiments the critical threshold is a force selected from an amount in pounds that is at least 2, 5, 10 20, 30, 40, 50, 60, 70, 80, 90, 100, 110, 120, 130, 140, 150, 160, 170, 180, 190 or 200 pounds.

The term "inhibited from rolling by means of the caster module" means that a brake is applied to at least one caster. Illustrative nonlimiting embodiments including: applying a clamp to a wheel or ball of a caster; and forcing a caster housing to make contact with a wheel or ball of a caster.

The term "rollable component" as used with respect to a caster means the portion of the caster that may rotate when in use, such as a wheel or ball.

The term "caster housing" means the portion of a caster within which a rollable component may rotate.

The term "line management collar" means a component that is attached to a central portion of the center mast, and that comprises at least one channel for receiving a tube and or power cord. The term line in this context applies to both tubes and power cords.

The term "line clasping feature" means a component that attaches to a tube or power cord. Illustrative nonlimiting examples of such features include hooks, clips, clamps, straps, cords for tying, slotted tubes, channel-containing blocks, and paired hook-and-loop textiles such as Velcro®.

The term "drawstring" means a connector that may be retracted to hold a tube or power cord with a reduced likelihood of entanglement. Illustrative nonlimiting examples of drawstring materials include strings, ropes, wires, cables, cords, tubes, chains, tapes and other films.

The term "retractably connected" as used with respect to a connection between a component and a drawstring means that slack in the drawstring may be taken up by an automated mechanism. In some embodiments the automated mechanism is a spring-loaded reel so as to maintain tension in the drawstring at all times. In certain embodiments the automated mechanism is ratcheted and act so that retraction of the drawstring occurs only upon deliberate triggering by a user.

The term "reel" as used with respect to retractable connection means a cylinder on which the drawstring can be wound and unwound. In certain embodiments the reel is spring-loaded. In some embodiments the reel is wound manually. In some embodiments the reel comprises a catch or ratchet so as to prevent motion of the drawstring in the tension-applying direction or alternatively the tension-releasing direction, in the absence of a manual override.

The term "rotatably connected" as used with respect to a collar on the center mast means that the collar is mounted on the mast in a way that permits the collar to be freely rotated at least partially around the circumference of a section of the mast.

The term "bezel" means a circular component having a female feature on the outside edge. The term "partial bezel" means that the female feature does not circle the entire component. The term "full bezel" means that the female feature does circle the entire component. The term "train" means a male feature on a component, where the train fits within and is captured by the bezel, and where the train is free to move freely through the female feature of the bezel.

The terms "hook fabric" and "loop fabric" have their usual and ordinary meaning. Illustrative nonlimiting examples include the types of fabric used in Velcro® connectors. The term "self-adhering strap" means a strap that contains both a hook fabric and a loop fabric. As used with respect to self-adhering straps, the terms "hook fabric portion" and "loop fabric portion" refers to the respective portions of the strap that comprise those respective fabrics.

The term "circularly distributed" as used with respect to components on a crown mean that the components are distributed at regular intervals as defined by a circle.

The term "rectangularly distributed" as used with respect to components on a crown mean that the components are distributed at intervals such that their innermost or alternatively outermost points fall within the perimeter of a square or other rectangle.

The invention may be further understood by consideration of the Figures, which show illustrative nonlimiting embodiments of the invention and its components.

FIG. 1 depicts a portion of an apparatus according to the invention not including a caster module. As shown in the Figure, the apparatus comprises center mast 110, crown 120 mounted at the top of the center mast; and 121 is an arm on the crown, where the arm bears a terminal hook. In the embodiment shown the crown has eight arms. Moreover the arms support fluid bags 125A and 125B, such as intravenous bags. Brackets 130 and 135 mounted on the center mast attach it to two peripheral handles 141 and 142, which respectively have channels 143 and 144 running through them, which may be milled channels, and which further respectively have clips 145A, 145B and 145C on handle 141 and clips 146A, 146B and 146C on handle 143, for the purpose of retaining a tube or power cord within the channel when it is in use. A power receptacle 150 is located on lower bracket 135. A central zone of center mast 110 features a hand brake handle 115.

Figure 2:
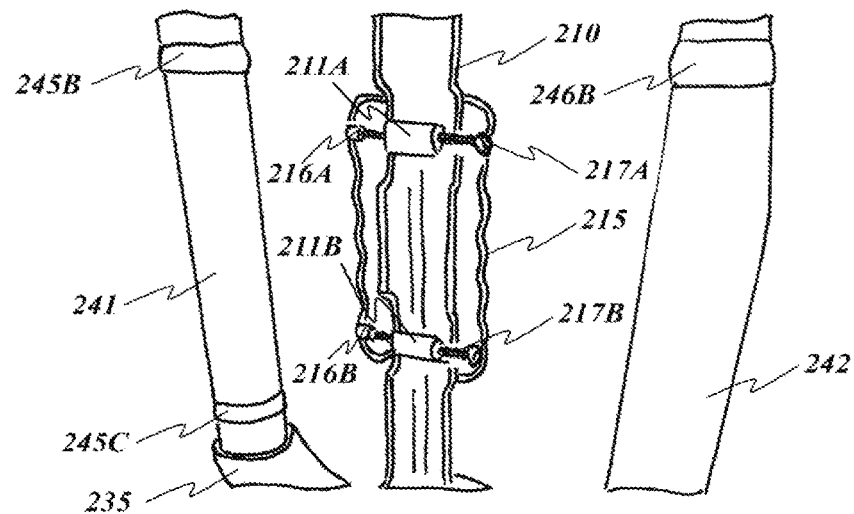
FIG. 2 is a caricature depicting a non-limiting embodiment of the invention, showing a cut-away section of a hand brake handle mechanism.

FIG. 2 depicts a section of the apparatus in perspective, in which peripheral handle 242 is nearer than peripheral handle 241 and the center mast 210 is between them. Clips 245B, 245C and 246B are provided to retain one or more tubes or power cord in channels within peripheral handles; to simplify the drawing the channels are not depicted. A portion of lower bracket 235 is also shown. Center mast 201 and hand brake handle 215 mounted on the center mast are shown in a cutaway view. Nut features 211A and 211B mounted on or integral to the inside of a tubular center mast 210 are capable of receiving screws or bolts 216A, 216B, 217A and 217B, such that a monolithic hollow molded handle or a molded handle in two parts may be fastened to the center mast by means of the screws or bolts. In an alternative embodiment nut features 211A and 211B are mounted on or integral to a rod not shown, that runs up through the center of a tube, where the center mast comprises both the rod and the tube, such that downward pressure applied on the brake handle drives not the tube but the rod downward; in such a design the screws or bolts must have a slot available so that the rod can travel freely for at least some discrete length in order to actuate braking.

Figure 3:
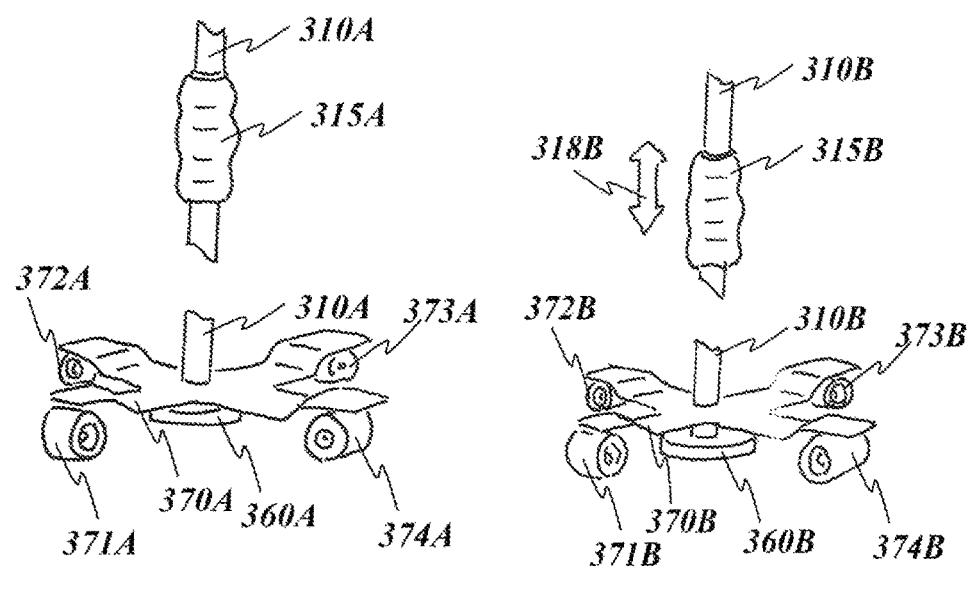
FIG. 3 is a caricature depicting a non-limiting embodiment of the invention, showing a braking mechanism.

FIG. 3 depicts sections of the invention apparatus when the center mast is in the raised position as on the left, allowing mobility of the apparatus, or in the lowered position as on the right, enabling braking by means of contact with a foot on the center mast with the floor. Here the center mast 310A and 310B is mounted by a hand brake handle 315A and 315B. The center mast passes through the housing of a caster module 370 A and 370B, having casters 371A, 372A, 373A and 374A as well as 371B, 372B, 373B and 374B. To simplify the figure, features such as the attachment of the casters to the rest of the caster module are not shown. When the center mast 310 A is raised, the foot 360A attached to its lower end is out of contact with the floor surface. When the center mast 310 B is lowered, the foot 360B attached to its lower end comes into contact with the floor surface and provide braking contact with the floor surface, particularly when the foot has a composition that is a friction-enhancing material. The mechanical actuation of the brake may be further assisted by other means such as supplementary mechanical leverage or a pneumatic or hydraulic component that is activated when the user deploys the brake.

Figure 4:
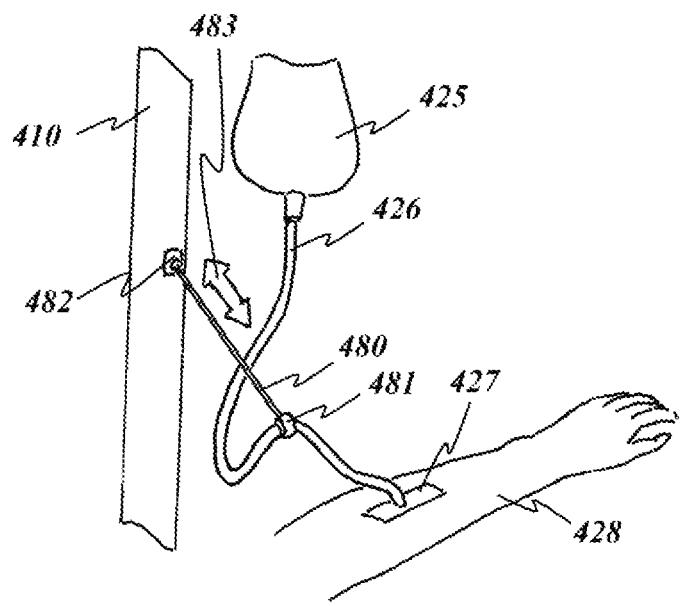
FIG. 4 is a caricature depicting a non-limiting embodiment of the invention, showing a drawstring manager for tubing.

FIG. 4 shows a portion of an apparatus according to the invention. There a center mast 410 has a draw string 481 that is under low tension and is retractable from a port or collar 482 and thus can readily be withdrawn reversibly as illustrated by directions of use 483. In its tension state the draw string lifts the tubing off the floor and bunches is near the mast. The other end of the draw string has a tube-holding feature 481 such as a clip, clamp, clasp, tie or strap that may be attached to the tube 426 of an intravenous bag 425. The fluid is delivered at an intravenous injection site 427 on a patient's arm 428. The collar 482 may optionally be equipped with a groove and train to permit rotation around a collar on the center mast by a spool for the draw string.

Figure 5:
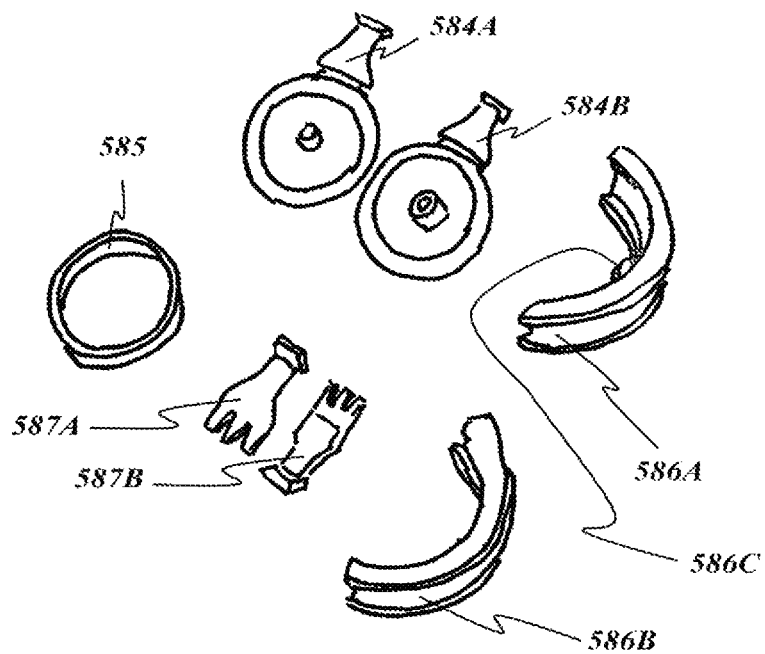
FIG. 5 is a caricature depicting a non-limiting embodiment of the invention, showing separately a drawstring spool, mating collar with an interior bezel, and a train that may tide or slide on the bezel.

FIG. 5 depicts an illustrative nonlimiting set of components for the fabrication of a suitable rotating collar including male 584A and female 584B halves for a spool housing, optionally with a spool cover 585. Two halves 586A and 586B of a mating collar for the center mast may be held in place against the center mast for instance by a tab 586C. Illustrative parts 587A and 587B may serve as a train for the exterior of the collar. The mating collar in this embodiment has an interior bezel around which the train may slide, and one viable form of the train is shown but the invention is not so limited. The form in both FIGS. 5 and 6 has the reel free-spinning on the end of the train.

Figure 6:
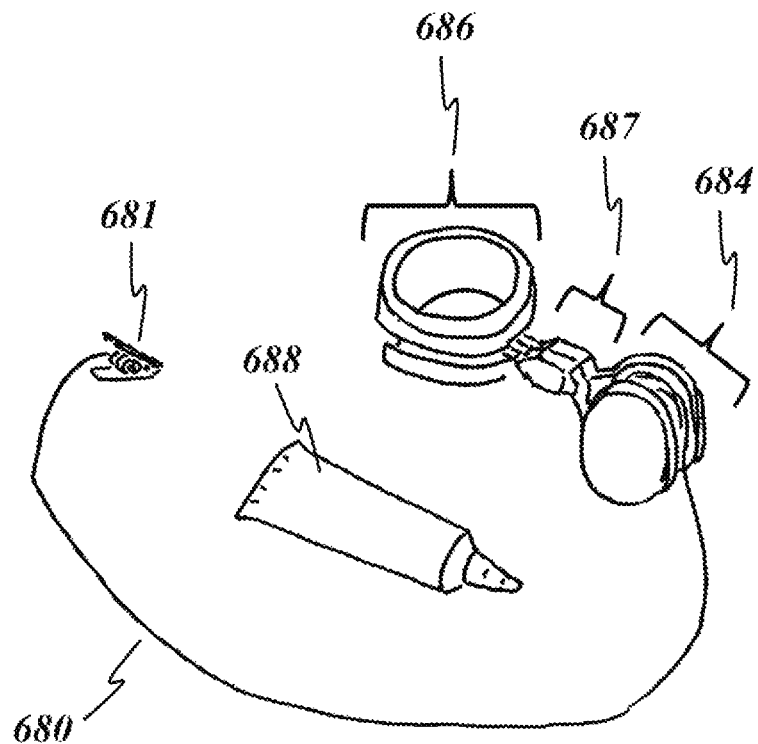
FIG. 6 is a caricature depicting a non-limiting embodiment of the invention, showing an assembly in which a collar is mated with a spool by means of a train that may rotate inside the collar.

FIG. 6 shows an illustrative nonlimiting assembly in which a clip 681 is located at the terminus of drawstring 680, which is wound about spool 684. A train 687 connected to the spool is captured by and may ride the circumference of a mating collar 686 that can encircle and attach to the center mast; the train may occupy an entire bezel or partial bezel. A lubricant 688 such as graphite, chalk, molybdenum sulfate, a petroleum-based lubricant or another type of lubricant may be used to facilitate the free rotation of the train around the collar.

Figure 7:
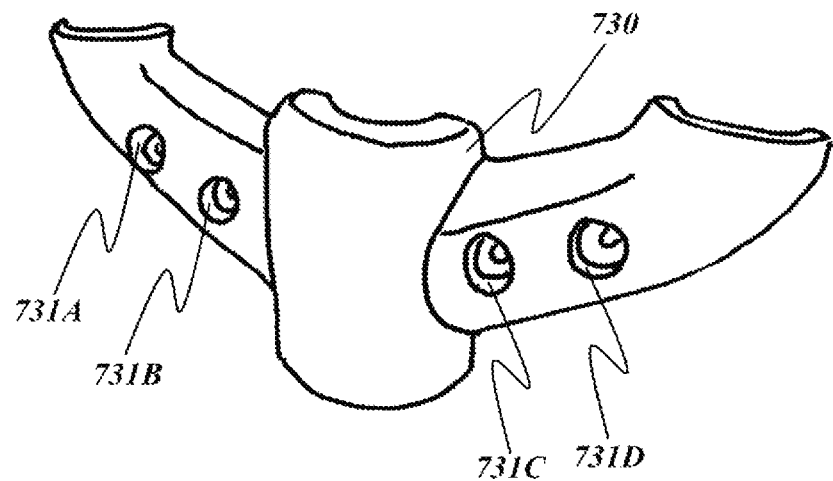
FIG. 7 is a caricature depicting a non-limiting embodiment of the invention, showing features of a bracket that may form either side of a handle.

FIG. 7 depicts an illustrative nonlimiting bracket design that may be used to attach the center mast to a peripheral handle. Here the bracket half 730 conforms to the shape and dimensions of one side of a center mast, and the wings of the bracket half permit combination with peripheral handles at its extremities. The bracket half may be attached by means of screws, nut-and-bolts, rivets, or other attachment means passing through shafts 731A, 731B, 731C and 731D. The design is also amenable to use with a snap fit and or adhesive.

Figure 8:
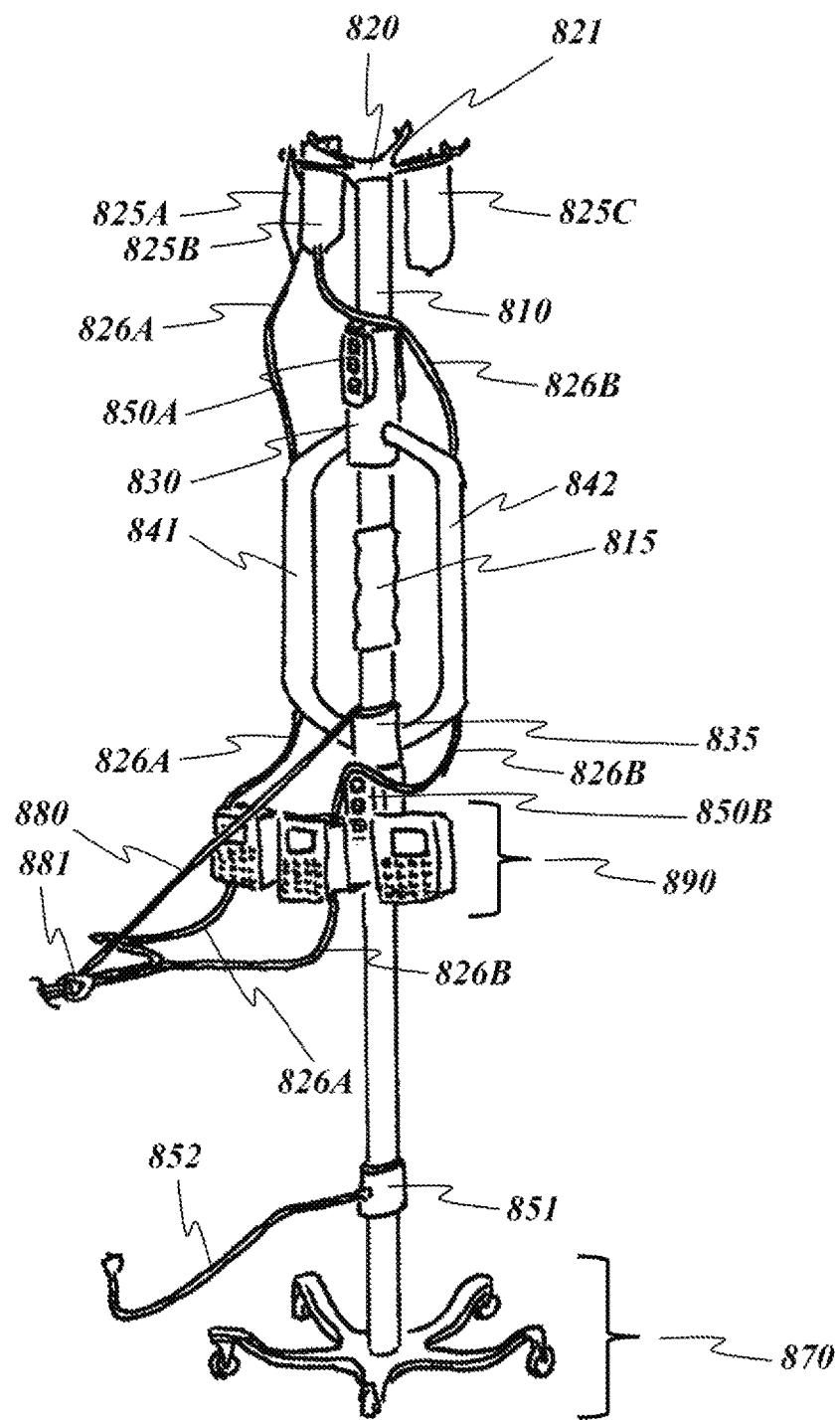
FIG. 8 is a caricature depicting a non-limiting embodiment of the invention, showing an assembled apparatus according to the invention.

FIG. 8 shows an illustrative nonlimiting apparatus in full with various components. As shown in the Figure, the apparatus comprises center mast 110, crown 120 mounted at the top of the center mast and having in this example eight arms; as seen for arm 821 on the crown, the arm bears a terminal hook. Moreover the arms support fluid bags 825A, 825B and 825C, such as intravenous bags. From bags 825A and 825B proceed tubes 826A and 826B respectively. Brackets 830 and 835 mounted on the center mast attach it to two peripheral handles 841 and 842, which respectively have channels running through them; to simplify the diagram those channels and their clips are not shown, however it will be noted that tubes 826A and 826B are shown to enter and exit the peripheral handles; slack in the tubes is taken up by a draw string 880 with a clip or clamp 881 around the tubes, and in this embodiment the other end of the draw string may be held or retracted at a collar or bracket 835. Power outlets 850A and 850B are mounted upon the brackets; in some embodiments the power outlets are integrated into the brackets. A power cord 852 is provided for use when the apparatus is stationary; it passes through and is retractable at a cord collar 851; here a power cable runs up inside of a hollow center mast from the cord collar to the power outlets. A hand brake handle 815 facilitates user braking of the apparatus. Caster module 870 has a plurality of caster and permits both rolling and braking. An instrument rack 890 is also shown; in some embodiments the instruments and or rack are mounted permanently directly on the center mast or a bracket; in others they are attached by temporary means; in still others they are attached by means including a quick-release mechanism.

Figure 9:
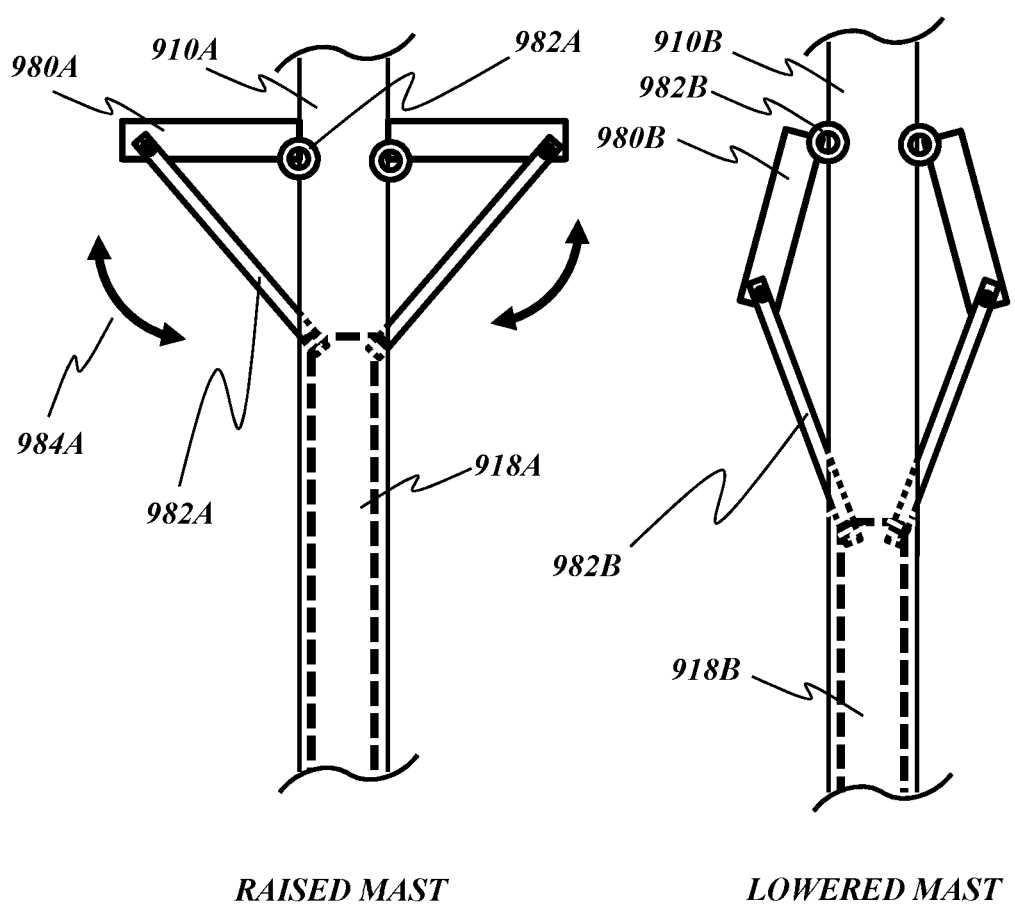
FIG. 9 is a caricature depicting a non-limiting embodiment of the invention, showing non-braking and braking states when a brake handle is turned to move a rod downward for a rod-in-tube mast configuration.

FIG. 9 depicts non-braking (raised-mast) and braking (lowered-mast) states when a brake handle is turned to move a rod downward for a rod-in-tube mast configuration in one embodiment. The center mast (910A and 910B) is a hollow tube, and its internal rod (918A and 918B) represent a rod-in-tube configuration. Lateral handles (980A and 980B) on the center mast are attached to the rod (by elements 982A and 982B). The handles are capable of turning (along a path denoted by arrow 984A) such that when the handles are turned downward they lower the rod relative to the tube. In FIG. 9 the broken lines for the rod and elements connected to it denote that those portions of the component are located within the tube. For the sake of visual clarity and simplicity, vertical slots at each side of the center mast are not depicted here; these allow elements 982A and 982B to reach from the rod to the handles, and to travel to the raised and lowered position, comparable to the slot that accommodates motion by internal nuts and bolts 211 of hand brake handle 215 to allow free travel of the rod in FIG. 2.

Figure 10:
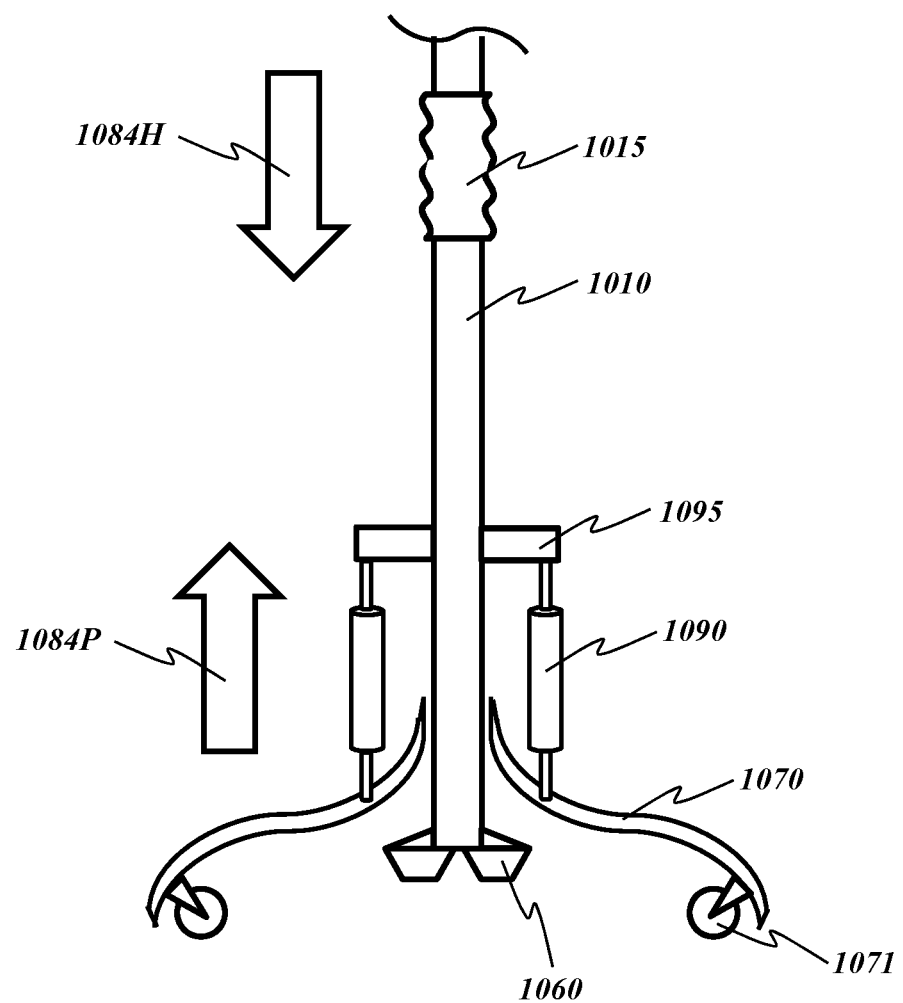
FIG. 10 is a caricature depicting a non-limiting embodiment of the invention, showing a brake that is actuated by a handle on a center mast, and use of pneumatic components to suspend the center mast and its feet out of contact with the floor surface.

FIG. 10 shows a brake that is actuated by a handle affixed on the center mast, and use of pneumatic components to suspend the center mast and its feet out of contact with the floor surface. There center mast 1010 has brake handle 1015 for which force is applied downward (direction 1084H) to actuate the brake. The center mast passes through caster module 1070, which has wheels in individual casters such as 1071. For the sake of visual clarity only two of the casters are shown. Feet such as 1060 are mounted at the bottom of the center mast to serve as braking surfaces on the ground, comparable to braking by use of the foot shown in FIG. 3. In FIG. 10 for the non-breaking state the feet are suspended above the ground level (the bottom of the wheels being understood to rest on the ground). Pneumatic components such as 1090 are affixed to the center mast by an affixing means such as 1095 and are also affixed at a separate site to the caster module, and provide mechanical force upward (as denoted by direction 1084P), thereby raising the upright center mast vertically relative to the caster module to keep its feet out of contact with the floor surface.

Figure 11:
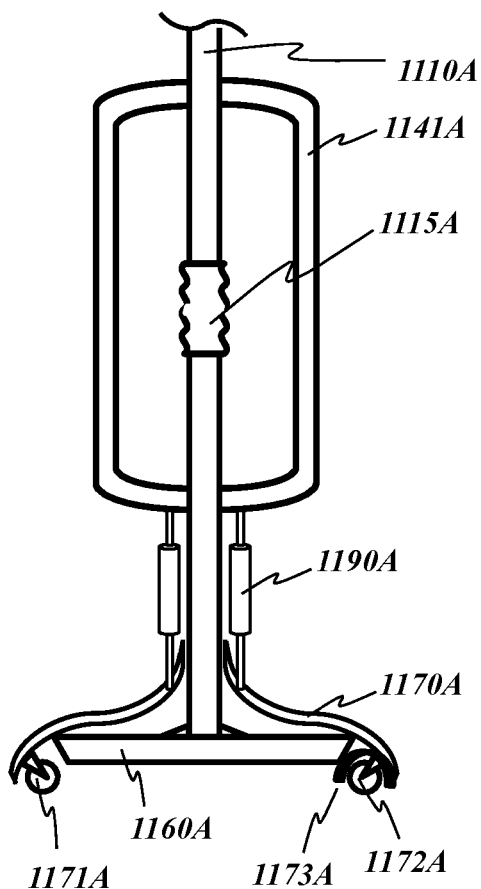
FIG. 11 is a caricature depicting a non-limiting embodiment of the invention, showing non-braking and braking states when a brake is actuated by clamping a wheel or caster housing.
Figure 11:
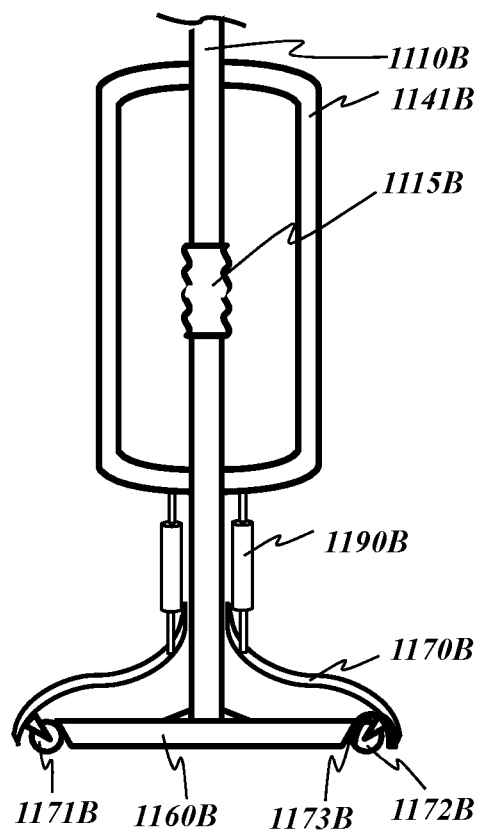

FIG. 11 shows an embodiment according to the invention in which a foot serves as an actuator or castor brake in lieu of or at the same time as acting as a friction brake with the ground. Here the raised and lowered states of the mast are compared. A hand brake handle (1115A and 1115B) and peripheral handles (1141A and 1141B) are affixed to the center mast (1110A and 1110B); in this embodiment any of these handles can be used for the application of downward force for braking purposes. The center mast passes through and is vertically mobile relative to the caster module (1170A and 1170B) and has a foot (1160A and 1160B). For the sake of visual clarity and simplicity only two of the casters are shown, and to illustrate variations in braking mechanism they are of different types. In one type of caster the wheel is exposed on the side toward the foot on the center mast (1171A and 1171B). In the other type of caster (1172A and 1172B), a caster housing—shown arc-like in FIG. 11—is interposed between the wheel and the foot. It can be seen that when the center mast is in the lowered state, i.e., when the brake is actuated, the foot clamps the exposed wheel directly (1171B) whereas for the wheel with a caster housing it compresses the housing against that wheel (1172B). In this embodiment pneumatic components 1190B serve to release the foot from the wheel and suspend the center mast when the brake is not in use.

The invention provides a combination of features that medical intravenous stands in the prior art lack. These include a brake, ergonomic design for supporting unsteady patients, channels and a multi-axis drawstring to manage tube and cords. The invention design minimizes tipping of the apparatus, tripping over cords, soiling and spoiling of tubes by contact with the floor, and the like. The invention is not limited to use with intravenous bags but can be used in addition or alternatively for support of components for other types of medical fluid management with bags and or tubes, for instance catheterization or other types of fluid transfer lines.

A variety of materials and designs may be used for the center mast. In certain embodiments 6061 raw stock aluminum tubes with a 1.5 inch diameter are employed.

Peripheral handles may be constructed, for example from milled or injected plastic, or from metal. In one embodiment they are held in place by two pairs of bracket halves that clasp together using symmetrical position pegs with opposing holes. Like brackets, hand brake handles may likewise be assembled from sections, e.g., in halves composed of molded plastic. In certain embodiments one or more brackets may house an electric socket fixture. In various embodiments the brackets and the hand brake handle are each assembled as one piece using notches in the center mast as slots to fit protrusions built on the mast side of the bracket or handle piece.

In certain embodiments a hand brake handle is attached to an internal mechanism to deploy a rubber lined foot by pushing a rod down through the middle of a center mast to make contact with the floor.

It is helpful though not required to employ a brake handle that has a grip, ergonomic design and an antimicrobial or easily cleanable surface. A particularly desirable brake handle grip would inhibit pathogens, facilitate patient use, be comfortable to the hand, and be suitable for many hand sizes.

A drawstring assembly is provided—optionally employing a retracting reel—that may be rotated up to 360° horizontally optionally with the aid of a collar that has inset grooves that may accommodate a train component. In combination with the drawstring's ability to rotate 360° in any vertical plane, this adaptability minimizes tangling of tubes and cords held by the drawstring, and further enables following the patient as they move at the outer allowed by the length of the tubing and or, if present, a power cord plugged into a wall. The pivot attached to a train is a helpful feature of this design.

From the description and claims herein, the invention and many useful permutations, variations, and derivatives of it will be apparent to the person having ordinary skill in the relevant arts, and are contemplated within the scope of the invention.

The invention claimed is:

1. An apparatus for support of components for transfer of fluids to or from medical patients, comprising:
   a) a caster module wherein:
      i) three or more casters are distributed about the caster module symmetrically relative to each other and equidistant from a virtual central point of the caster module;
      ii) a receiving collar defines a vertical central passage through the caster module when the caster module is horizontal, wherein that passage is symmetrically distributed about a virtual center line; and
      iii) the receiving collar is configured to receive and hold a mast in an upright orientation when the casters rest on a horizontal floor surface;
   b) an upright center mast wherein:
      i) the mast passes through and is slidably connected to the receiving collar of the caster module;
      ii) the bottom of the mast is mated with one or more feet and said one or more feet reside below the receiving collar of the caster module when the casters rest on a horizontal floor surface;
      iii) one or more peripheral handles are mounted on a central portion of the mast, wherein:
         A) at least one peripheral handle defines at least one channel for receiving at least one tube or power cord; and
         B) at least one power outlet is mounted on the center mast; and
      iv) a crown is mounted at the top of the mast and comprises a plurality of supports for hanging at least one bag of an intravenous fluid; and
   c) the support apparatus further comprises a brake assembly comprising:
      i) at least one hand brake handle, wherein at least one of the central portion of the mast and a peripheral handle has a hand brake handle mounted upon it;
      ii) a brake for application to at least one of a floor surface and a caster; and
      iii) a brake line that is connected to each of the hand brake handle and the brake.

2. The support apparatus of claim 1, further comprising a line management collar mounted on the center mast, wherein:
   a) said collar is connected to a first end of a drawstring;
   b) a second end of the drawstring is connected to a line clasping feature; and
   c) the connection to the drawstring is retractable for at least one of the collar and the line clasping feature.

3. The support apparatus of claim 2, wherein the line management collar is rotatably connected to the center mast by means of a train and at least a partial bezel.

4. The support apparatus of claim 2, wherein the retractable connection for the drawstring comprises a reel.

5. The support apparatus of claim 2, wherein the line clasping feature comprises a self-adhering strap comprising a hook fabric portion and a loop fabric portion.

6. The support apparatus of claim 1, wherein the supports for hanging comprised by the crown are circularly distributed.

7. The support apparatus of claim 1, wherein the supports for hanging comprised by the crown are rectangularly distributed.

8. The support apparatus of claim 1, wherein:
   a) the apparatus has a brake engagement mechanism comprising transfer of downward force from a hand brake handle to one or more feet on the center mast;
   b) the hand brake handle is affixed to the center mast;
   c) the center mast is vertically mobile relative to the caster module; and
   d) when the brake is not engaged a pneumatic component that is affixed at a first site to the center mast and at a second site to the caster module, suspends the center mast and its feet out of contact with the floor surface.

9. The support apparatus of claim 1, wherein:
   a) the apparatus has a brake engagement mechanism comprising transfer of downward force from a hand brake handle to a respective brake for at least one caster; and
   b) the hand brake handle is affixed to the center mast.

10. The support apparatus of claim 1, wherein:
    a) the apparatus has a brake engagement mechanism comprising transfer of downward force from a hand brake handle to a respective brake for at least one caster;
    b) the hand brake handle is affixed to a peripheral handle.

11. The support apparatus of claim 1, wherein a caster is equipped with a brake and the brake is actuated by clamping against a rollable component of the caster or compressing a caster housing against a rollable component of the caster.

12. The support apparatus of claim 1, wherein the mast has a rod-in-tube configuration and the rod of the mast is attached to a brake handle which, when turned while the support apparatus is upright, moves the rod downward relative to the tube of the mast.

\* \* \* \* \*